United States Patent [19]
Randall et al.

[11] 3,994,970
[45] Nov. 30, 1976

[54] 2-CHLOROETHYL PHOSPHONIC DIAMIDE

[75] Inventors: David I. Randall; Robert W. Wynn, both of Easton, Pa.

[73] Assignee: GAF Corporation, New York, N.Y.

[22] Filed: Nov. 16, 1971

[21] Appl. No.: 199,314

Related U.S. Application Data

[62] Division of Ser. No. 887,752, Dec. 23, 1969, Pat. No. 3,713,805.

[52] U.S. Cl. .................................. 260/551 P; 71/86
[51] Int. Cl.² .......................................... C07D 9/22
[58] Field of Search ................................. 260/551

[56] References Cited
UNITED STATES PATENTS

| | | | |
|---|---|---|---|
| 2,535,876 | 12/1950 | Stewart | 71/77 |
| 2,852,550 | 9/1958 | Godfrey | 260/551 |
| 3,671,212 | 6/1972 | Jaworski | 71/77 |
| 3,733,192 | 5/1973 | Harris et al. | 71/77 |

OTHER PUBLICATIONS

Chemical Abstracts, vol. 68, item 79601g (April 28, 1968) (Abstract of Neth. Patent 6615460).
Klement et al, Berichte, vol. 87, pp. 333–340 (1954).
Brewster, Organic Chemistry, p. 216, (1953).
Cook et al, Nature, vol. 218, pp. 974–975 (6/1968).
Houben–Weyl, Methoden der Organischen Chemie, vol. 12/1, p. 356 (1963).
Fluck, Topics in Phosphorus Chemistry (Grayson et al, editors) vol. 4, p. 329 (1967).

*Primary Examiner*—Henry R. Jiles
*Assistant Examiner*—R. W. Ramsuer
*Attorney, Agent, or Firm*—Walter C. Kehm; Marilyn J. Maue

[57] ABSTRACT

Plant growth regulating compound is 2-chloroethanephosphonic diamide of the formula:

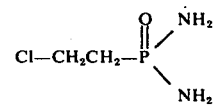

where the compound is prepared by the reaction of ammonia with 2-chloroethylphosphonyl dihalide and subsequently purified to remove ammonium halide by reaction with a secondary amine in chloroform.

1 Claim, No Drawings

2-CHLOROETHYL PHOSPHONIC DIAMIDE

This is a division of application Ser. No. 887,752, filed Dec. 23, 1969 now U.S. Pat. No. 3,713,805.

BACKGROUND OF THE INVENTION

1. Field of the Invention

This invention relates to 2-chloroethylphosphonic diamide, useful as a plant growth regulator, and processes for its preparation and purification.

2. Background of the Prior Art

The art is aware that certain phosphorus-containing compounds are useful as plant growth regulators. One of the most important phosphorus compounds of this type is 2-chloroethylphosphonic acid which has found importance as a plant growth regulator, particularly in the treatment of pineapples, soy beans and other plants to control their rate of growth. The present invention provides a new phosphorus-containing compound useful as a plant growth regulator not known heretofore, which compound has utility in this area equivalent to 2-chloroethylphosphonic acid. One of the primary characteristics of a product of this type is in the presence of the 2-chloroethyl group as this is important to the plant growth stimulating activity because it is believed that the action of the compound is due to the fact that it is absorbed by the plant and releases ethylene, a known plant regulator, in a form in which it can be used by the plant.

The art is aware of various substituted amides and diamides which have been prepared by reaction of an amine with a phosphonic acid dihalide. For example, in Chemical Abstracts, Vol. 66, page 54802, there is disclosed the reaction of ClCH$_2$CH$_2$OPCl$_2$ with diethylamine to yield ClCH$_2$CH$_2$PO=(NC$_2$H$_5$)$_2$ and ClCH$_2$CH$_2$OP=(NC$_2$H$_5$)$_2$. Also, in Chemical Abstracts, Vol. 42, page 4132, there is taught the reaction of aniline with chloroethanephosphonyl chloride to yield the dianiline derivative. However, none of these references show formation of the unsubstituted diamide or methods for its preparation. Moreover, none of the references show procedures for preparation of the compound in substantially pure form.

SUMMARY OF THE INVENTION

It is accordingly one object of this invention to provide the novel compound, 2-chloroethylphosphonic diamide, in highly purified form.

A further object of the invention is to provide an economical process by which this product may be produced and a method for its purification.

Other objects and advantages of the present invention will become apparent as the description thereof proceeds.

In satisfaction of the foregoing objects and advantages, there is provided by this invention a plant growth regulator of the following formula:

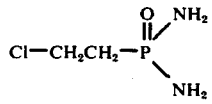

Also provided is a process for preparation of this compound by the reaction of ammonia with a 2-chloroethylphosphonyl dihalide and subsequent purification of the product to remove by-product ammonium halide by its reaction with a secondary amine in the presence of chloroform whereby the by-product ammonium halide reacts with the secondary amine to form gaseous ammonia which escapes to the atmosphere and secondary ammonium halide (amine hydrochloride) which is soluble in chloroform.

DESCRIPTION OF PREFERRED EMBODIMENTS

It has been found that the above-identified 2-chloroethylphosphonic diamide has unique activity as a plant growth regulator and may be applied to plants such as pineapples, soy beans, tomatoes, small grains and the like to regulate growth to thereby improve crop yields thereof. Thus, the compound may be stated to be a plant growth hormone as it operates to increase yields of the products mentioned as well as others.

The compound of this invention is soluble in varying degrees in water and so it can be applied to the plants in aqueous solutions composed wholly or partially of water; partial solutions include those formed of water and say acetone or methyl ethyl ketone. Any aqueous medium may be used provided that it is not toxic to the plant. Also, the compound may be absorbed on solid carriers such as vermiculite, attaclay, talc and the like for application in granular form. Dusts may also be used in which case the active ingredient will be diluted with clays or other powders, for example pyrophyllite, diatomaceous earth and attapulgite.

The compound of the invention can be applied to the plants at a concentration of from ½–10 lbs./Acre or higher. A preferred rate of application ranges from 2–5 lbs./Acre. The compound needs only to be applied to the plant in low volumes of water to achieve satisfactory initiation, and this is an important advantage of this invention. Whereas it is necessary to apply the known agents in large volumes of water, on the order of 200–400 gallons/Acre, even up to 1,000 gallons/Acre in the case of ethylene, to achieve initiation, it is possible to apply the compound of this invention in far lower volumes of water to achieve satisfactory flower initiation. For example, the compound of the present invention can be applied in 50 gallons of water at the rate of 1 lb./Acre to achieve 100% flower induction on pineapples of the Smooth Cayenne variety. The ability to apply the agent in a reduced volume of water is a great agronomic advantage because a larger acreage of plantation can be treated before recourse to a water supply is necessary, smaller equipment can be used and costs can be reduced generally.

The compound of this invention may be prepared by the reaction of 2-chloroethylphosphonyl dihalide of the following formula:

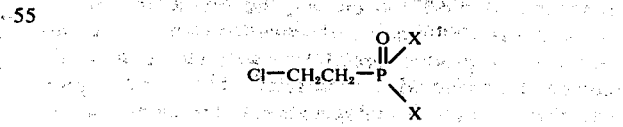

wherein X is halogen, preferably chlorine, but it may also be bromine, iodine or fluorine, with an excess of ammonia.

The reaction is conducted in the presence of a solvent which has preferably been dried to remove water prior to use. A preferred solvent to be employed in the process is chloroform but there may also be used solvents such as diethyl ether, dioxane, petroleum ether, aromatic hydrocarbons, (e.g. benzene, toluene, xylene, etc.), as well as mixtures thereof.

The reaction is conducted at atmospheric pressure and at a low temperature of about 0° to 40° C., preferably 10° to 35° C. Generally however, the reaction is conducted at about room temperature. In addition, in a preferred aspect, each of the reactants are mixed while contained in the solvent. Moreover, the ammonia reactant is preferably utilized in excess to insure completeness of reaction.

The process is preferably conducted by charging each of the reactants to a portion of the solvent, and the solutions contacted at the temperatures mentioned. In a preferred procedure, the solvent is saturated with ammonia gas and the starting 2-chloroethyl compound is then generally charged to the ammoniated solvent in a portion of the solvent. A stream of the ammonia is then continuously passed into the mixture.

As indicated the product of the invention is prepared by reacting an excess of ammonia with a 2-chloroethylphosphonyl dihalide. In this reaction, there is formed the desired diamide product in good yield but there is also formed some ammonium halide (e.g. ammonium chloride) as an excess of ammonia is present to combine with the halogen from the starting material. The crude mixture of diamide and ammonium chloride or other halide may be used in the treatment of plants as described hereinabove since the ammonium chloride is quite harmless to plants and animals in the concentrations required and indeed may even act as a fertilizer for furnishing nitrogen to the plants.

It is often desirable and sometimes necessary however to separate the diamide from the ammonium halide and the present invention provides a simple procedure for effecting this separation in a separate embodiment. According to this invention, the diamide and ammonium halide may be easily separated by reacting the ammonium halide, while in admixture with the diamide, with a secondary amine in chloroform. Suitable secondary amines which may be employed include the dialkylamines (wherein the alkyl groups contain 1 to about 7 carbon atoms), diarylamines (e.g. diphenylamine), diaralkylamines (e.g. dibenzylamine), dialkarylamines (e.g. ditolylamine), and mixtures thereof. A highly preferred amine is diethylamine because of its ready availability.

In this reaction, the diamide/ammonium chloride mixture and about a stoichiometric quantity of secondary amine are charged to the chloroform and gently refluxed until dissolution is complete. There is thus formed a secondary ammonium chloride (e.g. diethyl ammonium chloride with diethylamine), which is soluble in chloroform and gaseous ammonia which escapes from the solution. On cooling the secondary ammonium chloride (amine hydrochloride) remains in solution and the product precipitates as a crystalline solid and can be collected as by filtration. This result is quite surprising as dehydrohalogenation of the carbon skeleton of the diamide would be expected to occur resulting in the formation of vinylphosphonic diamide.

The following examples are provided to illustrate the compound and processes of the present invention.

EXAMPLE I

2-Chloroethylphosphonic Diamide

There was charged to a reaction flask 800 cc. dry chloroform. The solvent was saturated with dry ammonia gas at room temperature and while continuing a slow stream of ammonia through the solution, there was added dropwise a solution of 18.2 grams (0.1 mole) 2-chloroethanephosphonic dichloride in 100 cc. dry chloroform.

The product was collected in a sintered glass funnel and quickly placed in a vacuum desiccator where it was dried at room temperature. The mixture of product and ammonium chloride weighed 22.0 grams.

EXAMPLE II

Purification of 2-Chloroethylphosphonic Diamide

Into an Erlenmeyer flask there was charged 5.0 grams of the product from Example I, 3.7 grams diethylamine and 80 cc. of dry chloroform. While stirring on the magnetic stirrer, the mixture was gently refluxed until dissolution was complete. The solution was stored in the refrigerator overnight and the product then collected and dried. Yield = 1.5 grams, mp. = 109°–112° C.

| Analysis | Calc'd. | Found |
|---|---|---|
| % Cl | 24.91 | 24.57 |
| % N | 19.65 | 20.08 |

EXAMPLE III

2-Chloroethylphosphonic Diamide

A charge of 500 cc. dry benzene was saturated with dry ammonia gas and while continuing a slow stream of ammonia through the solution at room temperature, there was added dropwise a solution of 18.2 grams (0.1 mole) 2-chloroethanephosphonic dichloride in 100 cc. dry benzene. The product was collected on a sintered glass funnel and quickly placed in a vacuum desiccator where it was dried to constant weight at room temperature. The solid weighed 23.3 grams.

This product can be freed from ammonium chloride by following the procedure described in Example II.

The invention has been described herein with reference to certain preferred embodiments. However, it is not to be considered as limited thereto as obvious variations thereon will occur to those skilled in the art.

What is claimed is:

1. 2-Chloroethanephosphonic diamide of the formula:

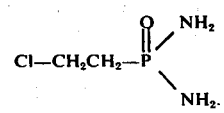

* * * * *